United States Patent [19]
Kosley, Jr. et al.

[11] Patent Number: 5,777,108
[45] Date of Patent: Jul. 7, 1998

[54] GALANTHAMINE DERIVATIVES AS ACETYLCHOLINESTERASE INHIBITORS

[75] Inventors: Raymond W. Kosley, Jr., Bridgewater; Larry Davis, Sergeantsville; Veronica Taberna, Union, all of N.J.

[73] Assignee: Hoechst Marion Roussel, Inc., Cincinnati, Ohio

[21] Appl. No.: 445,921

[22] Filed: May 22, 1995

Related U.S. Application Data

[62] Division of Ser. No. 137,440, Oct. 15, 1993.

[51] Int. Cl.$^6$ .......................... C07D 491/06; C07B 41/04
[52] U.S. Cl. ................................................. 540/546
[58] Field of Search .................................. 540/546

[56] References Cited

PUBLICATIONS

Harvey, Pharmac. Ther. 68, 113 (1995).
Han, European J. Med. Chem 27, 673(1992).
Bores, Drugs of the Future 21, 621(1996).
Green, "Protective Groups in Organic Synthesis", 2nd Ed. (1991) p. 186.
FDC Report (Pink Sheet) Sep. 30, 1996, p. 9.
Script #2028, May 26, 1996, p. 27.
Koft, Tetrahedron 43, 5775 (1987).
Feutrill, Tet. Letters 1970, p. 1327.
Feutrill, Aus. J. Chem. 25, 1719(1972).
Kendo, J. Org. Chem 50, 727(1985).
Hoffman, J. Org. Chem. 56, 2081 (1991).
Majetich Tetrahedron Letters 34, 445 (1993).
Smith, Tetrahedron Letters 36, 4283 (1985).

Primary Examiner—Mark L. Berch
Attorney, Agent, or Firm—Edlyn S. Simmons; Barbara V. Maurer

[57] ABSTRACT

This application relates to compounds of the formula

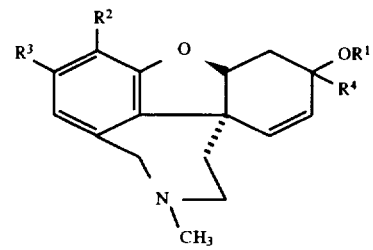

wherein $R^1$, $R^2$, $R^3$ and $R^4$ are defined within, which compounds are useful for the treatment of memory dysfunction characterized by decreased cholinergic function, pharmaceutical compositions containing the compounds and methods for making and using the compounds.

9 Claims, No Drawings

GALANTHAMINE DERIVATIVES AS ACETYLCHOLINESTERASE INHIBITORS

This is a division of a pending prior application, Ser. No. 08/137,440, filed Oct. 15, 1993.

This application relates to compounds of the formula

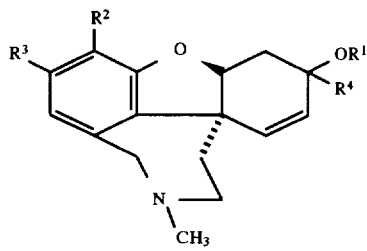

wherein $R^1$ is hydrogen, $(C_1-C_{12})$alkylcarbonyl, $(C_1-C_{12})$alkoxycarbonyl, mono$(C_1-C_{12})$alkylaminocarbonyl or di$(C_1-C_8)$alkylaminocarbonyl;

$R^2$ is hydrogen, $(C_3-C_{12})$alkenylcarbonyloxy, $(C_3-C_{12})$cycloalkylcarbonyloxyl, $(C_3-C_{12})$cycloalkylaminocarbonyloxy, $(C_3-C_{12})$alkynylcarbonyloxy, $(C_3-C_{12})$cycloalkyl$(C_1-C_{12})$alkylcarbonyloxy, oxygen containing heterocyclyloxy, oxygen containing heterocyclylcarbonyloxy, sulfur containing heterocyclyloxy, sulfur containing heterocyclylcarbonyloxy, nitrogen containing heterocyclyloxy, nitrogen containing heterocyclylcarbonyloxy, haloalkylsulfonyloxy, $(C_1-C_6)$alkylsilyloxy;

$R^3$ is hydrogen, halo or $(C_1-C_4)$alkyl;

$R^4$ is hydrogen or $(C_1-C_6)$alkyl;

with the proviso that $R^1$ and $R^2$ are not both hydrogen when $R^3$ and $R^4$ are hydrogen;

all geometric, and optical and stereoisomers thereof, or a pharmaceutically acceptable addition salt thereof;

which are useful for alleviating various memory dysfunctions such as found in Alzheimer's disease.

This invention also provides a pharmaceutical composition useful for alleviating various memory dysfunctions characterized by decreased cholinergic function which comprises a compound of the invention in an amount sufficient to affect cholinergic function and a pharmaceutically acceptable carrier. This invention further provides a method for treating the effects of Alzheimer's disease which comprises treating a patient with a pharmaceutically effective amount of a compound of the invention.

Unless otherwise stated or indicated, the following definitions shall apply throughout the specification and appended claims.

Then term "alkyl" shall mean a straight or branched alkyl group of the stated number of carbon atoms. Examples include, but are not limited to methyl, ethyl, n-propyl, iso-propyl, n-butyl, isobutyl, sec-butyl, t-butyl, and straight and branched chain pentyl, hexyl, heptyl, octyl, nonyl, decyl, undecyl, dodecyl and dodecyl.

The term "halo" shall mean chloro, fluoro, bromo and iodo.

The term "aryl" shall mean phenyl having 0, 1, 2 or 3 substituents independently selected from the group of $(C_1-C_6)$alkyl, $(C_1-C_6)$alkoxy, $(C_1-C_6)$alkylcarbonyl, halo or trifluoromethyl.

The term "cycloalkyl" shall mean a cycloalkyl group of from 3 to 12 carbon atoms such as for example, cyclopropyl, cyclobutyl, cyclopentyl, cyclohexyl, cycloheptyl and cyclododecyl and including multiple ring alkyls such as for example, norbornanyl, adamantyl, cis-bicyclo[3.3.0] octanyl, camphoryl, oxotricyclo[2.2.1.0$^{2,6}$]heptane-7-yl and 3-noradamantyl.

The term "nitrogen-containing heterocycle" shall mean a 5 or 6 membered saturated or partially unsaturated ring, optionally fused to another saturated, unsaturated or aromatic ring, having at least one nitrogen atom which is also bonded to the additional portion of the molecule. Examples include morpholine, tetrahydroisoquinoline, piperidine, pyrrolidine, pyridine and the like.

The term "oxygen-containing heterocycle" shall mean a 5 or 6 membered saturated or partially unsaturated ring, optionally fused to another saturated, unsaturated or aromatic ring, having at least one oxygen atom which is also bonded to the additional portion of the molecule. Examples include furan and tetrahydrofuran and the like.

The term "sulfur-containing heterocycle" shall mean a 5 or 6 membered saturated or partially unsaturated ring, optionally fused to another saturated, unsaturated or aromatic ring, having at least one sulfur atom which is also bonded to the additional portion of the molecule. Examples include thiophene and the like.

In a preferred embodiment are compounds of the formula

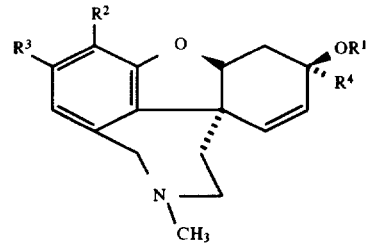

wherein $R^1$ is hydrogen, $(C_1-C_{12})$alkylcarbonyl, $(C_1-C_{12})$alkoxycarbonyl;

$R^2$ is hydrogen, $(C_3-C_{12})$alkenylcarbonyloxy, $(C_3-C_{12})$alkynylcarbonyloxy, $(C_3-C_{12})$cycloalkylcarbonyloxy, $(C_3-C_{12})$cycloalkyl$(C_1-C_{12})$alkylcarbonyloxy, $(C_3-C_{12})$cycloalkylcarbonyloxy, cycloalkylaminocarbonyloxy, halo$(C_1-C_6)$ alkylsulfonyloxy, $(C_1-C_6)$alkylsilyloxy, pyridyloxy, thiomorpholinocarbonyloxy, furanylcarbonyloxy, thienylcarbonyloxy, tetrahydrofuranylcarbonyloxy, furanyloxy, thienyloxy, pyrrolidinylcarbonyloxy, tetrahydrofuranyloxy, piperadinylcarbonyloxy, azepincarbonyloxy, morpholinocarbonyloxy or tetrahydroisoquinolinylcarbonyloxy;

$R^3$ is hydrogen or halo;

$R^4$ is hydrogen or $(C_1-C_6)$alkyl;

with the proviso that $R^1$ and $R^2$ are not both hydrogen when $R^3$ and $R^4$ are hydrogen;

and all geometric, optical and sterioisomers and pharmaceutically acceptable addition salts thereof.

More preferably $R^1$ is hydrogen, $(C_1-C_{12})$alkylcarbonyl or $(C_1-C_{12})$alkoxycarbonyl; $R^2$ is $(C_3-C_{12})$ alkenylcarbonyloxy, $(C_3-C_{12})$alkynylcarbonyloxy, $(C_3-C_{12})$cycloalkylcarbonyloxy, $(C_3-C_{12})$cycloalkyl $(C_1-C_{12})$alkylcarbonxyloxy, pyridyloxy, furanyloxy, morpholinocarbonyloxy or tetrahydroisoquinolylcarbonyloxy; $R^3$ is hydrogen or bromine; and $R^4$ is hydrogen or methyl.

Most preferably $R^1$ is hydrogen, $R^2$ is cyclopropylcarbonyloxy, cyclobutylcarbonyloxy, cyclohexylcarbonyloxy, methylcyclohexylcarbonyloxy, adamantylcarbonyloxy, adamantylmethylcarbonyloxy, 2-methylpropenylcarbonyloxy, 2-propynylcarbonyloxy, cycloheptylaminocarbonyloxy, cyclohexylaminocarbonyloxy, morpholinocarbonyloxy or tetrahydroisoquinolylcarbonyloxy; and $R^3$ and $R^4$ are hydrogen.

The compounds of the invention are prepared from the appropriate optical isomer of galanthamine as described more fully below and shown in Scheme I.

In the case where $R^5$ is pyridyl or other heterocycle, the compound of Formula V is typically reacted with an appropriate halopyridine or other haloheterocycle in the presence of base such as for example potassium t-butoxide. The reaction is typically carried out in a non-protic polar solvent such as, for example, dimethylformamide at from about room temperature to about 150° C., preferably about 110° C.

SCHEME 1

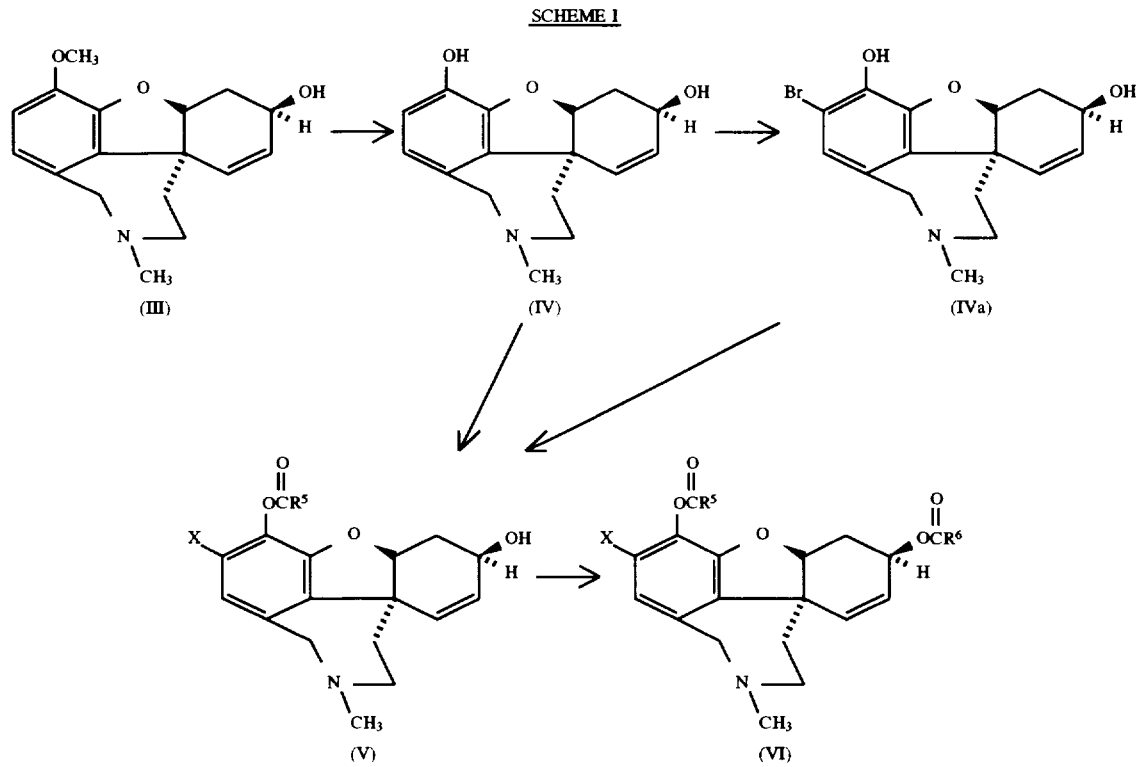

The intermediate 6-demethylgalanthamine of Formula IV, a known compound was prepared in a novel process by treating the galanthamine of Formula III with an alkylthio salt of sodium, potassium, lithium or cesium, preferably ($C_1$–$C_4$)alkylthio salts of sodium and lithium, most preferably EtSLi, or EtSNa. The reaction is typically carried out in a polar nonprotic solvent such as dimethylformamide (DMF) or N-methylpyrrolidone (NMP) or a protic solvent such as butanol or pentanol, preferably DMF or NMP at from about 80° C. to about 135° C., preferably from about 90° C. to about 125° C.

The compound of Formula VI wherein $R^5$ is ($C_3$–$C_{12}$) cycloalkylaminocarbonyl is prepared by treating the compound of Formula IV with the appropriate isocyanato compound $R^4$NCO. The reaction is carried out in an aprotic solvent such as, for example, tetrahydrofuran in the presence of base such as, for example, potassium carbonate at from about –10° C. to about 30° C. for from about 0.5 hours to about 4 hours.

In the case where $R^5$ is cycloalkylcarbonyl, alkenylcarbonyl or alkynylcarbonyl, the compound of Formula V is typically reacted with an appropriate carboxylic anhydride in the presence of a base such as 4-dimethylaminopyridine (DMAP) or carboxylic acid chloride in the presence of a base such as 1,8-diazabiscyclo[5.4.0]undec-7-ene (DBU). The reactions are typically carried out in a non-protic solvent such as, for example, chloroform at from about 0° C. to about 50° C., preferably from about 15° C. to about 30° C.

In the case where $R^5$ is alkylsilyl, the compound of Formula V is typically reacted with the appropriate alkylsilyl halide at from about 0° C. to about 80° C., preferably at about room temperature. The reaction is typically carried out in a non-protic solvent such as dimethylformamide or tetrahydrofuran.

In the case where $R^5$ is haloalkylsulfonyl, the compound of Formula V is typically reacted with the appropriate sulfonic acid anhydride in a solvent such as pyridine. Alternatively the reaction can be carried out at about –60° C. to about –50° C. in dichloromethane or chloroform in the presence of a base such as diisopropylethylamine. The reaction is typically carried out at from about –10° C. to about 50° C., preferably from about 0° C. to about room temperature.

The compound of Formula VI can be prepared from the compound of Formula V. In the case where $R^6$ is alkylamino or arylamino, a solution of the appropriate isocyanate and the compound V in a nonprotic solvent such as tetrahydrofuran in a sealed tube at from about 55° C. to about 85° C. for from about 24 hours to about 120 hours, preferably at from about 60° C. to about 70° C. for from about 60 hours to about 80 hours.

In the case where $R^6$ is alkyl or aryl, the compound of Formula V is reacted with the appropriate carboxylic acid or anhydride under the conditions described above to obtain the compound of Formula VI.

In the case where X is Br, the compound of Formula IV is treated with bromine in the presence of an amine such as t-butylamine to obtain the brominated compound. The bromine is first added to the t-butylamine at from about −20° C. to about −30° C., then the reaction mixture is cooled to about −80° C. to about −70° C. and the galanthamine compound is added. The reaction is typically carried out in a nonpolar organic solvent such as for example toluene. Following addition of galanthamine the mixture is allowed to warm from about −80° C. to about room temperature over from about 6 hours to about 10 hours, preferably about 8 hours.

In the case where $R^2$ of Formula I is hydrogen, the haloalkylsulfonyl compound of Formula V is typically reacted with palladium acetate and triphenylphosphine followed by triethylamine and formic acid. The reaction is typically carried out in a polar solvent such dimethylformamide at from about room temperature to about 100° C., at about 60° C. to about 70° C.

In the case where $R^4$ of Formula I is alkyl, typically the appropriate narwedine compound is reacted with the appropriate alkylmagnesium bromide in the presence of cerium (III) chloride. The reaction is typically carried in a nonprotic solvent such as tetrahydrofuran at from about −10° C. to about room temperature, preferably at about 0° C.

The compounds of Formula I of the present invention can be used for the treatment of various memory dysfunctions characterized by decreased cholinergic function, such as Alzheimer's disease. The compounds of the present invention are advantageous because they are less toxic and/or more potent than the related compounds known in the art. In addition, the 6-O-demethyl ester and carbonate derivatives of this invention can cleave to yield 6-O-demethylgalanthamine, a known acetylcholinesterase inhibitor.

This utility is manifested by the ability of these compounds to inhibit the enzyme acetylcholinesterase and thereby increase acetylcholine levels in the brain.

The ability to inhibit acetylcholinesterase was determined by the photometric method of Ellman et al., Biochem. Pharmacol. 7,88 (1961). Results of acetylcholinesterase inhibition for some of the compounds of this invention are presented in Table I along with those for reference compounds.

TABLE I

| Acetylcholinesterase Inhibition Assay | |
|---|---|
| Compound | $IC_{50}$ μM CHE I |
| (6-O-Demethyl)-6-O-(1,2,3,4-tetrahydroisoquinolin-2-yl)-carbonyl]-galanthamine hydrochloride | 0.0009 |
| Tacrine | 0.32 |

This utility can also be ascertained by determining the ability of these compounds to restore cholinergically deficient memory in the Dark Avoidance Assay. In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compounds, resulting in a greater interval before re-entry into the dark compartment.

The test results are expressed as the percent of a group of animals in which the effect of scopolamine is blocked, as manifested by an increased interval between being placed in the test chamber and re-entering the dark compartment. Results of Dark Avoidance Assay for some of the compounds of this invention are presented in Table II along with a result for a reference compounds.

TABLE II

| Example No. | SDDA Dose (mg/kg, s.c.) | Percent of Animals with Scopolamine Induced Memory Deficit Reversal |
|---|---|---|
| (6-O-Demethyl)-6-O-(1,2,3,4-tetrahydroisoquinolin-2-yl)-carbonyl]-galanthamine hydrochloride | 0.003 | 27 |
| Tacrine | 0.31 | 33 |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 5% to about 70% of the weight of the unit. The amount of active compound in such compositions is such that a suitable dosage will be obtained. Preferred compositions and preparations according to the present invention are prepared so that an oral dosage unit form contains between 1.0–200 milligrams of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above-type, a liquid carrier such as a fatty oil. Other dosage unit forms may contain other various materials which modify the physical form of the dosage unit, for example. as coatings. Thus, tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 200 milligrams of active compound.

The solutions or suspensions may also include the following components: a sterile diluent such as water for injection, saline solution, fixed oils, polyethylene glycols, glycerine, propylene glycol or other synthetic solvents; antibacterial agents, such as benzyl alcohol or methyl parabens; antioxidants such as ascorbic acid or sodium bisulfite; chelating agents such as ethylenediaminetetraacetic acid; buffers such as acetates; citrates or phosphates and agents for the adjustment of tonicity such as sodium chloride or dextrose. The parenteral multiple dose vials may be of glasser plastic.

The following Table III and examples will further illustrate this invention but are not intended to limit it in any way. In Table III typical compounds of the instant invention are listed. The melting points are of hydrochloride salts unless otherwise indicated. Following Table III, representative illustrative preparations of compounds of the invention are described.

TABLE III

| Ex. No. | R¹ | R² | R³ | R⁴ | m.p. °C. |
|---|---|---|---|---|---|
| 1 | H | OH | H | H | 225–229** |
| 2 | H | OC(=O)—N(naphthyl) | H | H | 258–260 |
| 3 | H | OCNH(cycloheptyl) | H | H | 224–226 |
| 4 | H | OCNH(cyclohexyl) | H | H | 238–240 |
| 5 | H | OH | Br | H | 128–141* |
| 6 | H | OC(=O)—N(morpholino) | H | H | 263–265d |
| 7 | H | OC(=O)-cyclopropyl | H | H | 244–245d |
| 8 | H | OC(=O)-cyclobutyl | H | H | 200–203 |
| 9 | H | OC(=O)-(4-methylcyclohexyl) | H | H | 256–258d |
| 10 | H | OC(=O)-adamantyl | H | H | 258–260d |
| 11 | H | OCCH₂-adamantyl | H | H | 253–255 |
| 12 | H | —OC(=O)CH=C(CH₃)₂ | H | H | 247d |
| 13 | H | —OC(=O)C≡CCH₃ | H | H | 191–195 |
| 14 | H | OC(=O)-pyridyl | H | H | 250–251d |
| 15 | H | OS(=O)₂CF₃ | H | H | 219–220 |
| 16 | H | OSi(CH₃)₂C(CH₃)₃ | H | H | 199d |
| 17 | H | OSi(CH₂CH₃)₃ | H | H | 128–130 |
| 18 | H | OSi(CH(CH₃)₂)₃ | H | H | 235d |
| 19 | H | OSi(CH₃)₃ | H | H | 173–174 |
| 20 | H | H | H | H | 242–244 |
| 21 | H | OCH₃ | H | CH₃ | 237–240 |

*Lit. m.p. 220–222
**isolated as free base

EXAMPLE 1

6-O-Demethylgalanthamine

To a stirred solution of 20 ml of dry DMF at –40° under nitrogen was added 0.57 ml (0.48 g) of ethanethiol. The mixture was stirred for several minutes at –40° to –30° after which 2.84 ml of 2.5M BuLi in hexanes was added slowly by syringe at –40° to –50°. The solution was then allowed to warm to room temperature over 15 minutes, heated to 50° under aspirator vacuum and again cooled to 30°. To the solution was added a solution of 0.57 g of galanthamine in 5.7 ml of dry DMF. The solution was stirred at 95°–100° for 2 hours and subsequently at 100°–105° for 3 hours, allowed to cool to room temperature and concentrated to an oil. The oil was dissolved in chloroform shaken with $NH_4Cl$, made basic with aq $NaHCO_3$ and extracted four times with $CHCl_3$. The pH of the aqueous layer was then adjusted to 9–10 with $NH_4OH$ and again extracted four times with chloroform. The combined organic extracts were dried ($Na_2SO_4$), filtered and concentrated to an oil. The oil was dissolved in degassed 5% methanol/chloroform and flash chromatographed on silica gel eluting with the same solvent system followed by 10% methanol/chloroform to provide a beige solid. The material was dissolved in acetone and allowed to crystallize overnight to provide 0.298 g of 6-O-demethylgalanthamine, m.p. 225°–229°.

Analysis:

Calculated for $C_{16}H_{19}NO_3$: 70.31% C 7.01% H 5.12% N

Found: 70.14% C 7.29% H 4.96% N

EXAMPLE 2

(6O-Demethyl)-6-O-(1,2,3,4-tetrahydroisoquinolin-2-yl)carbonyl]-galanthamine hydrochloride To a stirred suspension of 0.494 g of 6-O-demethylgalanthamine in 7 ml of dry dichloromethane was added 0.311 g of 1,1'-carbonyldiimidazole. The mixture was stirred at room temperature for 1 hour, cooled in an ice bath and 0.35 ml of acetic acid was added followed by 0.27 ml of 1,2,3,4-tetrahydroisoquinoline. The mixture was allowed to warm to room temperature and stirred at room temperature for 15 hours. The solution was cooled in an ice bath, poured into cold saturated $NaHCO_3$, extracted with dichloromethane, washed with water and concentrated to an oil. The material was dissolved in ethyl acetate/ether and the hydrochloride salt precipitated by addition of ethereal hydrogen chloride to provide 0.346 g of a white solid, m.p. 258°–260°.

Analysis:

Calculated for $C_{26}H_{28}N_2O_4 \cdot HCl$: 66.59% C 6.23% H 5.97% N

Found: 66.21% C 6.26% H 5.90% N

EXAMPLE 3

6O-Demethyl-6-O-(cycloheptylaminocarbonyl) galanthamine hydrochloride

To a mixture of 0.81 g of 6-O-demethylgalanthamine and 0.82 g of milled potassium carbonate was added 13.5 ml of dry THF via a syringe. The suspension was cooled to 0° C. after which 0.60 ml of cycloheptyl isocyanate was added slowly by syringe. The mixture was allowed to stir at 0° C. for 30 minutes and at room temperature for 45 minutes. The solution was poured onto a flash chromatography column, packed with silica gel and 3% methyl alcohol:chlorofonn, and eluted with the same solvent followed by 5% methyl alcohol:chloroform. The product-containing fractions were combined and concentrated to provide a white solid weighing 1.28 g. The solid was dissolved in dichloromethane, diluted with ethyl ether and the hydrochloride salt precipitated by addition of ethereal hydrogen chloride to provide 1.07 g of 6-O-demethyl-6-O-(cycloheptylaminocarbonyl)-galanthamine hydrochloride, m.p. 224°–226° C.

Analysis:

Calculated for $C_{24}H_{30}N_2O_4 \cdot HCl$: 64.20% C 7.41% H 6.24% N

Found: 63.78% C 7.47% H 6.17% N

EXAMPLE 4

6-O-Demethyl-6-O-(cyclohexylaminocarbonyl) galanthamine hydrochloride

To a stirred suspension of 0.8 g of 6-O-demethylgalanthamine, 0.8 g of milled potassium carbonate and 14 ml of THF in an ice bath was added 0.48 ml of cyclohexylisocyanate. The suspension was stirred at ice bath temperature for ½ hour and at room temperature for ½ hour. The mixture was then filtered onto a flash silica gel column packed with 3% methanol/chloroform and flash chromatographed eluting with the same solvent system followed by 5% methanol/chloroform. Concentration of the product-containing fractions provided an oil which was dissolved in ether and the hydrochloride salt precipitated by addition of ethereal HCl. The material was isolated by filtration and dried to provide 0.637 g of a white solid. Trituration/crystallization from ethanol provided analytically pure 6-O-demethyl-6-O-(cyclohexylaminocarbonyl)galanthamine hydrochloride, m.p. 238°–240° C.

Analysis:

Calculated for $C_{23}H_{30}N_2O_4 \cdot HCl$: 63.51% C 7.18% H 6.44% N

Found: 63.32% C 7.18% H 6.28% N

EXAMPLE 5

7-Bromo-6-O-demethylgalanthamine

To a stirred solution of 1.38 ml (0.966 g) of t-butylamine in 36 ml of azeotripically dried toluene at −20° to −30° C. was added dropwise 0.34 ml (1.05 g) of bromine such that the temperature remained between −20° to −30° C. The solution was then cooled to −70° to −75° C. and a solution of 3.0 g of 6-demethylgalanthamine in 15 ml of DMF was added slowly such that the temperature did not rise above −70° C. The solution was stirred for 2 hours at −70° to −78° C. and subsequently allowed to warm slowly to room temperature over 6 hours. The solution was again cooled to 0° C., poured into ice/$NaHCO_3$/water, and extracted with chloroform. The aqueous fraction was saturated with NaCl and extracted 3 times with chloroform. The chloroform extracts were dried ($Na_2SO_4$), filtered and concentrated to an oil which was purified by HPLC, employing a Water Prep 500 Instrument and eluting with 3% methanol/chloroform, followed by 5% methanol/chloroform. The pure product-containing fractions were combined and concentrated to provide 1.83 g (47.3% based on 6-demethylgalanthamine, 78.9% based on bromine, the limiting reagent). Crystallization from acetone provided analytically pure 7-bromo-6-O-demethyl galanthamine, m.p. 138°–141° C.

Analysis:

Calculated for $C_{16}H_{18}BrNO_3$: 54.56% C 5.15% H 3.98% N

Found: 54.62% C 5.50% H 3.61% N

EXAMPLE 6

6-O-Demethyl-6-O-(morpholinocarbonyl) galanthamine hydrochloride

To a stirred suspension of 0.80 g of 6-O-demethylgalanthamine in 11.2 ml of dichloromethane was added 0.50 g of 1,1'-carbonyldiimidazole. The mixture was stirred at room temperature for 1 hour and cooled in an ice bath. To the mixture was added 0.57 ml of acetic acid followed by 0.31 ml of morpholine at 0° C. The mixture was allowed to stir at room temperature for 3.5 hours and cooled once again to 0° C. The mixture was poured into a cold saturated solution of sodium bicarbonate and extracted twice with chloroform. The organic layers were combined, dried over $Na_2SO_4$, filtered and and concentrated to a yellow oil. The oil was dissolved in 3% methanol:chloroform and pipetted onto a flash chromatography column, packed with silica gel and 3% methanol:chloroform and eluted with the same solvent system, followed by 5% methanol:chloroform. The product-containing fractions were combined and concentrated to provide 0.86 g of an oil, which was dissolved in ethyl ether:chloroform and the hydrochloride salt was precipitated by addition of ethereal hydrogen chloride to provide 0.65 g of 6-O-demethyl-6-O-(morpholinocarbonyl) galanthamine hydrochloride as a white solid. The solid was recrystallized from acetonitrile:isopropyl alcohol, to provide material of m.p. 263°–265° C. (dec).

Analysis:

Calculated for $C_{21}H_{26}N_2O_5 \cdot HCl$: 59.64% C 6.44% H 6.62% N

Found: 59.60% C 6.09% H 6.72% N

EXAMPLE 7

6-O-Demethyl-6-O-(cyclopropanecarbonyl) galanthamine hydrochloride

To a stirred mixture of 0.80 g (2.92 mmol) of 6-O-demethylgalanthamine in 8 ml of dry chloroform was added 0.44 ml (2.94 mmol) of 1,8-diazabicyclo[5.4.0]undec-7-ene. The mixture was stirred at 0° C. for 10 minutes after which was added 0.29 ml (3.19 mmol) of cyclopropanecarbonyl chloride by syringe. The mixture was warmed to room temperature and stirred at this temperature for 2 hours, poured into a cold saturated solution of sodium bicarbonate and extracted twice with chloroform. To the aqueous layer was added sodium chloride after which it was extracted twice with chloroform. The organic layers were combined, dried over sodium sulfate, filtered, and concentrated to provide a yellow oil. The oil was dissolved in chloroform, pipetted onto a flash chromatography column packed with silica gel and 3% methanol:chloroform and eluted with the same solvent system followed by 5% methanol:chloroform. The pure, product-containing fractions were combined and concentrated to provide 0.76 g (2.23 mmol, 76%) of a white solid. The solid was dissolved in diethyl ether and the hydrochloride salt precipitated by addition of ethereal hydrogen chloride to provide 0.56 g (1.65 mmol; 56%) of 6-O-demethyl-6-O-(cyclopropanecarbonyl)galanthamine hydrochloride, m.p. 244°–245° C. (dec.).

Analysis:

Calculated for $C_{20}H_{23}NO_4 \cdot HCl$: 63.57% C 6.40% H 3.71% N

Found: 63.29% C 6.39% H 3.74% N

EXAMPLE 8

6-O-Demethyl-6-O-(cyclobutanecarbonyl) galanthamine hemihydrate hydrochloride

To a stirred suspension of 1.00 g (3.66 mmol) of 6-O-demethylgalanthamine in 8.0 ml of dry chloroform was added 0.55 ml (3.67 mmol) of 1,8-diazabicyclo-[5.4.0]-undec-7-ene. The suspension was stirred at 0° C. for 10 minutes after which was added 0.47 g (4.00 mmol) of cyclobutanecarbonyl chloride. The reaction mixture was warmed to room temperature and stirred at this temperature for 3 hours after which it was poured into a cold, saturated solution of sodium bicarbonate. The mixture was extracted once with chloroform and the aqueous layer was treated with sodium chloride and extracted twice with chloroform. The organic layers were combined, dried over sodium sulfate, filtered, and concentrated to an oil. The oil was dissolved in chloroform and pipetted onto a flash chromatography column, packed with silica gel and 3% methanol:chloroform and eluted with the same solvent system, followed by 5% methanol:chloroform. The appropriate fractions were combined and concentrated to provide a solid weighing 0.71 g (1.77 mmol; 48%). The solid was dissolved in diethyl ether and chloroform and the hydrochloride salt precipitated by addition of ethereal hydrogen chloride to give 6-O-demethyl-6-O-(cyclobutanecarbonyl)galanthamine hemihydrate hydrochloride, m.p. 200°–203° C.

Analysis:

Calculated for $C_{21}H_{25}NO_4 \cdot 0.5H_2O \cdot HCl$: 62.92% C 6.79% H 3.49% N Found: 62.68% C 6.84% H 3.43% N

EXAMPLE 9

6-O-Demethyl-6-O-(1-methylcyclohexanecarbonyl) galanthamine hydrochloride

To a stirred suspension of 0.37 g (2.63 mmol) of 1-methyl-1-cyclohexanecarboxylic acid in 1.0 ml of chloroform was added 0.54 g (2.61 mmol) of 1,3-dicyclohexylcarbodiimide dissolved in 1.0 ml of chloroform, followed by 0.71 g (2.62 mmol) of 6-O-demethylgalanthamine, and 3.17 g (2.59 mmol) of 4-dimethylaminopyridine dissolved in 1.5 ml of chloroform. The mixture was stirred at room temperature overnight after which it was poured into a cold saturated solution of sodium bicarbonate and extracted twice with chloroform. To the aqueous layer was added sodium chloride after which it was extracted twice with chloroform. The organic layers were combined, dried over sodium sulfate, filtered, and concentrated to a yellow oil. The oil was dissolved in chloroform, filtered onto a flash chromatography column, packed with silica gel and 3% methanol:chloroform and eluted with the same solvent system, followed by 5% methanol:chloroform. The pure, product-containing fractions were combined and concentrated to a white solid weighing 0.49 g (1.25 mmol; 48%). The solid was dissolved in diethyl ether and the hydrochloride salt precipitated by addition of ethereal hydrogen chloride to provide 6-O-demethyl-6-O-(1-methylcyclohexanecarbonyl)galanthamine hydrochloride, m.p. 256–258d.

Analysis:

Calculated for $C_{24}H_{31}NO_4HCl$: 66.42% C 7.43% H 3.23% N

Found: 66.66% C 7.47% H 3.17% N

EXAMPLE 10

6-O-Demethyl-6-O-[(adamantan-1-yl)carbonyl] galanthamine hydrochloride

To a stirred solution of 0.59 g (3.28 mmol) of 1-adamantanecarboxylic acid in 1.5 ml of chloroform was added 0.68 g of 1,3-dicyclohexylcarbodiimide dissolved in 0.5 ml of chloroform, followed by 0.90 g (3.28 mmol) of 6-O-demethylgalanthamine, and 0.40 g of 4-dimethylaminopyridine dissolved in 0.5 ml of chloroform. The reaction mixture was allowed to stir at room temperature for 5 hours after which it was filtered onto a flash chromatography column, packed with silica gel and 3% methanol:chloroform and eluted with the same solvent system, followed by 5% methanol:chloroform. The pure, product-containing fractions were combined and concentrated to a white solid weighing 0.67 g (1.54 mmol; 47%). The solid was dissolved in chloroform and diluted with diethyl ether and the hydrochloride salt precipitated by addition of ethereal hydrogen chloride. Recrystallization from acetonitrile:isopropanol followed by drying at 78° C., under high vacuum, provided 6-O-demethyl-6-O-|(adamantan-1-yl)carbonyl|galanthamine hydrochloride, m.p. 258°–260° C. (dec).

Analysis:

Calculated for $C_{27}H_{33}NO_4 \cdot HCl$: 68.70% C 7.26% H 2.97% N

Found: 68.46% C 7.48% H 2.87% N

EXAMPLE 11

6-O-Demethyl-6-O-|(adamantan-1-yl)methylcarbonyl|galanthamine hydrochloride

To a stirred suspension of 0.71 g (3.67 mmol) of 1-adamantaneacetic acid in 2.5 ml of chloroform was added 0.75 g (3.67 mmol) of 1,3-dicyclohexylcarbodiimide dissolved in 1.0 ml of chloroform, followed by 1.00 g (3.66 mmol) of 6-O-demethylgalanthamine in 2.0 ml of chloroform and 0.45 g (3.67 mmol) of dimethylaminopyridine. The mixture was stirred for 2 hours after which it was filtered onto a flash chromatography column, packed with silica gel and 3% methanol:chloroform and eluted with the same solvent system, followed by 5% methanol:chloroform. The appropriate fractions were combined and concentrated to a white solid weighing 1.16 g (2.58 mmol; 70%). The solid was dissolved in diethyl ether and the hydrochloride salt precipitated by addition of ethereal hydrogen chloride to provide 0.90 g (1.86 mmol; 51%) of 6-O-demethyl-6-O-|(adamantan-1-yl)methylcarbonyl|galanthamine hydrochloride, m.p. 253°–255° C. (dec).

Analysis:

Calculated for $C_{28}H_{35}NO_4 \cdot HCl$: 69.19% C 7.47% H 2.88% N

Found: 68.93% C 7.51% H 2.85% N

EXAMPLE 12

6-O-Demethyl-6-O-(2-methyl-1-propenylcarbonyl)galanthamine hydrochloride

To a cold solution of 6-O-demethylgalanthamine (2.0 g, 0.007 mole), triethylamine (1.10 ml, 0.007 mole) and 4-dimethylaminopyridine (0.01 g, 0.0001 mole) in 70 ml of dichloromethane, was added dropwise a solution of 3,3-dimethylacryloyl chloride (0.8 ml, 0.007 mole) in 10 ml of dichloromethane. After stirring at ambient temperature for 3 hours, the mixture was added to a silica gel column and eluted with 3% methanol/dichloromethane via HPLC. The desired fractions were combined and then evaporated to give a white solid, 1.6 g (64%), m.p. 74°–75° C. A solution of the solid in ether was adjusted to pH 1 with ethereal-HCl, and the resultant white solid was collected and dried to give 1.2 g (45%) of product, m.p. 247° C. (dec.).

Analysis:

Calculated for $C_{21}H_{25}NO_4 \cdot HCl$: 64.36% C 6.69% H 3.57% N

Found: 64.18% C 6.73% H 3.51% N

EXAMPLE 13

6-O-Demethyl-6-O-(propynylcarbonyl)galanthamine hydrochloride

To a stirred mixture of 0.61 g (7.31 mmol) of 2-butynoic acid in 3.0 ml of chloroform was added 1.51 g (7.31 mmol) of 1,3-dicyclohexylcarbodiimide dissolved in 2.0 ml of chloroform, followed by 1.99 g (7.31 mmol) of 6-O-demethylgalanthamine, 2.0 ml of chloroform, and 0.09 g (0.73 mmol) of 4-dimethylaminopyridine dissolved in 0.5 ml of chloroform. The reaction mixture was stirred at room temperature for 0.5 hours after which it was poured into a cold, saturated solution of sodium bicarbonate and extracted once with chloroform. To the aqueous layer was added sodium chloride after which it was extracted twice with chloroform, and the combined chloroform extracts, dried over sodium sulfate, filtered, and concentrated to a brown oil. The oil was dissolved in chloroform, filtered onto a flash chromatography column, packed with silica gel and 3% methanol:chloroform, and eluted with the same solvent system, followed by 5% methanol:chloroform. The pure, product-containing fractions were combined and concentrated to a yellow oil weighing 1.84 g (5.41 mmol; 74%). The oil was dissolved in diethyl ether and the hydrochloride salt precipitated by addition of ethereal hydrogen chloride to provide 1.00 g (2.67 mmol; 37%) of 6-O-demethyl-6-O-(propynylcarbonyl)galanthamine hydrochloride, m.p. 191–195 (dec.).

Analysis:

Calculated for $C_{20}H_{21}NO_4 \cdot HCl$: 63.91% C 5.90% H 3.73% N

Found: 63.38% C 5.73% H 3.59% N

EXAMPLE 14

6-O-Demethyl-6-O-(pyridin-2-yl)galanthamine hydrochloride

A mixture of 2.00 g (7.33 mmol) of 6-O-demethylgalanthamine and 822.1 mg (7.33 mmol) of potassium-t-butoxide in 20 ml DMF was stirred for 10 minutes. The mixture was heated to 110° C. and 0.630 ml of 2-fluoropyridine (7.33 mmol) was added. The reaction mixture was stirred at 110° C. for 2 hours at which point 177.8 mg (1.47 mmol) of KOtBu, dissolved in 0.2 ml DMF, and 0.126 ml (1.47 mmol) of 2-fluoropyridine were added. The mixture was stirred for an additional 2 hours at 110° C. After 2 hours an additional 177.8 mg (1.47 mmol) of KOtBU, dissolved in 0.2 ml DMF, and 0.126 ml (1.47 mmol) of 2-fluoropyridine were added and the mixture was stirred again for 2 hours at 110° C. The reaction was then allowed to cool and then poured into a 200 ml ice/water mixture. The aqueous solution was saturated with sodium chloride and extracted three times with 150 ml of chloroform. The organic layers were combined, dried over sodium sulfate, filtered, and concentrated. The resulting oil was chromatographed by preparative HPLC using 1% methanol:chloroform. The product containing fractions were concentrated to provide 1.32 g (3.79 mmol, 51.7%) of product which was recrystallized from ethyl acetate in two crops to yield 692 mg of a white solid. The solid was dissolved in 10 ml chloroform:10 ml diethylether and ethereal hydrogen chloride was added. The precipitated salt was dried 2 hours at 80° C. and 2 hours at 111° C. to provide 679 mg (25.2%) of 6-O-demethyl-6-O-(pyridin-2-yl)galanthamine hydrochloride, m.p. 250°–251° C. (dec).

Analysis:

Calculated for $C_{21}H_{22}N_2O_3 \cdot HCl$: 63.71% C 6.11% H 7.08% N

Found: 63.86% C 6.01% H 7.03% N

EXAMPLE 15

6-O-Demethyl-6-O-trifluoromethylsulfonylgalanthamine hydrochloride

A stirred solution of 2.0 g (7.33 mmol) of 6-O-demethylgalanthamine in 8 ml of dry pyridine was cooled in an ice/salt bath. To the solution was added slowly dropwise over several minutes 1.23 ml (2.07 g, 7.34 mmol) of triflouromethanesulfonic acid anhydride. The solution was allowed to warm to room temperature and stirred for 16 hours. The solution was poured into water/ice/chloroform, dried ($Na_2SO_4$), filtered and concentrated to an oil. The material was dissolved in chloroform and flash chromatographed on silica gel, eluting with 1% methanol/chloroform followed by 2% methanol/chloroform. The pure product-containing fractions were combined and concentrated to provide 0.625 g of a yellow solid. The material was dissolved in ether and the hydrochloride salt precipitated by addition of ethereal HCl, isolated by filtration, washed with ether and dried to provide 6-O-demethyl-6-O-trifluoromethylsulfonylgalanthamine hydrochloride, m.p. 219°–220° C.

Analysis:

Calculated for $C_{17}H_{18}F_3NO_5S \cdot HCl$: 46.21% C 4.33% H 3.17% N

Found: 45.79% C 4.29% H 2.86% N

EXAMPLE 16

6-Demethyl-6-O-(t-butyldimethylsilyl)galanthamine hydrochloride

To a cold solution of 6-O-demethylgalanthamine (3.0 g, 11 mmol) and imidazole (1.9 g, 28 mmol) in 30 ml of dimethylformamide, was added dropwise a tetrahydrofuran solution of t-butyldimethylsilyl chloride (1M solution in THF, 12 ml, 12 mmol).

After stirring at ambient temperature for twenty hours, the mixture was poured into water, stirred for 5 minutes, and then extracted with ethyl acetate (3×). The organic layer was washed with water, saturated sodium chloride solution, and dried over anhydrous $MgSO_4$.

After filtering, the solvent was evaporated to give a yellow oil, 4 g; which was eluted on a silica gel column with 3% methanol/dichlorofmethane via HPLC. The desired fractions were combined and evaporated to afford a white solid, 2.5 g (60%), m.p. 88°–90° C. This material was dissolved in methanol, acidified to pH 1 with etheral HCL, and then diluted with ether. The resultant white precipitate was collected and dried to give 1.7 g (36%) of the product as a colorless solid, m.p. 199° C. (dec.).

Analysis:

Calculated for $C_{22}H_{33}NO_3Si \cdot HCl$: 62.31% C 8.08% H 3.30% N

Found: 62.00% C 8.20% H 3.21% N

EXAMPLE 17

6-O-Demethyl-6-O-(triethylsilyl)galanthamine

To a cold solution of 6-O-demethylgalanthamine (3.0 g, 11 mmol) and imidazole (1.9 g, 28 mmol) in 35 ml of dimethylformamide, was added dropwise a solution of chlorotriethylsilane (1M solution in THF, 12 ml, 12 mmol).

After stirring at ambient temperature for 20 hours, the mixture was poured into water, stirred for 5 minutes, and then extracted with ethyl acetate (2×). The organic layer was washed with water, saturated NaCl solution, and then dried over anhydrous $MgSO_4$. Filtering and concentration of the filtrated afforded a yellow oil, 4.0 g (90%), which was eluted on a silica gel column with 5% methanol/dichlorofmethane via HPLC. The desired fractions were combined and then evaporated to give a white solid, 2.4 g (57%), m.p. 128°–130° C. This material was recrystallized from ether to give white crystals, 1.4 g (30%), m.p. 128°–130° C.

Analysis:

Calculated for $C_{22}H_{33}NO_3Si$: 68.17% C 8.58% H 3.61% N

Found: 67.81% C 8.71% H 3.60% N

EXAMPLE 18

6-O-Demethyl-6-O-(triisopropylsilyl)galanthamine hydrochloride

To a cold solution of 6-O-demethyl-galanthamine (3.0 g, 11 mmol) and imidazole (1.9 g, 28 mmol) in 30 ml of dimethylformamide, was added dropwise a solution of triisopropylsilyl chloride (2.6 ml, 12 mmol) in 5 ml of diemthylformamide.

After stirring at ambient temperature for 20 hours, the mxiture was poured into 200 ml of water, stirred for 5 minutes and then extracted with ethyl acetate (2×100 ml). The organic layer was washed with water, saturated NaCl solution, and dried over anhydrous $MgSO_4$.

After filtering the filtrate was evaporated in vacuo to a yellow oil (~4 g), which was eluted on a silica gel column with 3% methanol/dichloromethane via HPLC. The desired fractions were combined and evaporated in vacuo to a yellow solid, 3.5 g, m.p. 53°–56° C.

A 1.0 g sample of this material was dissolved in methanol, acidified to pH 1 with ethereal-HCl and then diluted with ether. The resultant white precipitate was collected and dried to give 1.0 g (90%) of the products as colorless solid, m.p. 235° C. (dec).

Analysis:

Calculated for $C_{25}H_{39}NO_3Si \cdot HCl$: 64.41% C 8.65% H 3.01% N

Found: 64.15% C 8.42% H 2.84% N

EXAMPLE 19

6-O-Demethyl-6-O-(trimethylsilyl)galanthamine

To a cold solution of 6-O-demethyl-galanthamine (3.0 g, 11 mmol) and imidazole (1.9 g, 28 mmol) in 30 ml of dimethylformamide was added chlorotrimethylsilane (1.0M solution in DCM, 12 ml, 12 mmol) dropwise.

After stirring at ambient temperature for 20 hours, the mixture was poured into 200 ml of water, stirred for 5 minutes, and then extracted with ethyl acetate (2×100 ml). The organic layer was washed with water, saturated NaCl solution and then dried over anhydrous $MgSO_4$.

After filtering, the filtrate was evaporated in vacuo to a yellow oil, 3.0 g. This oil was eluted on a silica gel column with 5% methanol/dichloromethane via HPLC. The desired fractions were combined, then evaporated to a white solid, 1.4 g (37%), m.p. 173°–174° C.

17

Analysis:

Calculated for C₁₉H₂₇NO₃Si: 66.04% C 7.88% H 4.05% N

Found: 65.63% C 7.89% H 3.98% N

EXAMPLE 20

6-Demethoxygalanthamine hydrochloride

To a stirred solutin of 1.0 g (2.47 mmol) of recrystallized 6-O-demethyl-6-O-trifluoromethylsulfonylgalanthamine and 33 mg (0.126 mmol of triphenylphosphine in 40 ml of dry DMF was added 55.5 mg (0.248 mmol) of palladium (II)acetate, followed by 1.05 ml of triethylame and 0.185 ml of 96% formic acid. The solution was stirred at 60°–65° C. for 10 hours, then allowed to cool to room temperature, poured into ice/NaHCO₃, extracted with chloroform, concentrated to an oil and flash chromatographed on silica gel, eluting with 1%, 2% and 5% methanol/chloroform, respectively. The product-containing fractions were combined and concentrated to provide 0.53 g of solid. The material was dissolved in chloroform, diluted with ether, filtered and the hydrochlorided salt precipitated by addition of ethereal HCl. The material was crystallized from acetonitrile to provide 0.315 g of a solid, mp 242°–244° C.

Analysis:

Calculated for C₁₆H₁₉NO₂·HCl: 65.41% C 6.86% H 4.77% N

Found: 65.31% C 6.78% H 4.67% N

EXAMPLE 21

3-(alpha-Methyl)galanthamine hydrochloride

Cerium (III)chloride (1.63 g, 6.63 mmol) was heated at 130°–140° C. for 2 hours then cooled and 22 ml of dry THF was added and the suspension was stirred overnight at room temperature. The suspension was then cooled in an ice/salt water bate and 2.2 ml of 3.0M methyl magnesium bromide in diethyl ether was added. The mixture was stirred at ice bath temperature for 1.5 hours followed by the addition of a suspension of 1.25 g (4.39 mmol) of narwedine in 12.5 ml of THF. The resulting suspension was stirred for 0.5 hour and then poured into ice/NH₄Cl/chloroform. The mixture was basified with sodium bicarbonate, extracted with chloroform, dried (N₂SO₄), filtered and concentrated to an oil. The oil was chromatographed by flash chromatography on silica gel eluting with chloroform followed by 2% methanol/chloroform/saturated ammonium hydroxide. The product containing fractions were combined and concentrated to provide 0.91 g of an oil. The oil was dissolved in ethyl acetate and flash chromatographed on silica gel, eluting with 2%, 5% and 10%, respectively, isopropyl alcohol/ethyl acetate (saturated ammonium hydroxide). The product containing fractions were combined and concentrated to provide an oil which was dissolved in ether, cooled and ethereal HCl was added. The suspension was filtered and the residue was washed with ether and dried for 2 hours at 80° C. The resulting solid was triturated with hot acetonitrile, centrifuge and dried to provide 0.20 g of product, m.p. 237°–240° C.

Analysis:

Calculated for C₁₈H₂₃NO₃·HCl: 63.99% C 7.16% H 4.15% N

Found: 63.83% C 7.15% H 4.00% N

It should be understood that this specification and examples are set forth by way of illustration and not limitation and that various modifications and changes may be made without departing from the spirit and scope of the present invention as defined by the appended claims.

We claim:

1. A process for the preparation of the compound of the formula

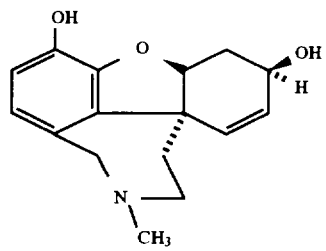

which comprises treating the galanthamine of formula III

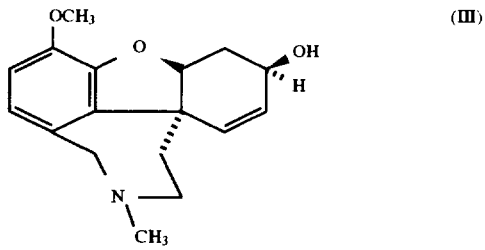

(III)

with an alkylthio salt of sodium, potassium, lithium or cesium, in a polar protic solvent at a temperature of from about 80° C. to about 135° C.

2. The process of claim 1 which is carried out in butanol or pentanol.

3. The process of claim 1 wherein the salt is a sodium or lithium salt.

4. The process of claim 1 wherein the salt is EtSLi or EtSNa.

5. The process of claim 1 which is carried out at from about 90° C. to about 125° C.

6. A process for the preparation of the compound of the formula

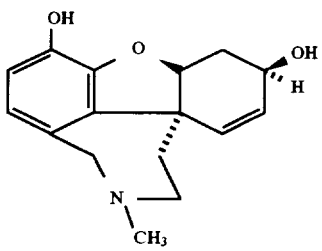

which comprises treating the galanthamine of formula III

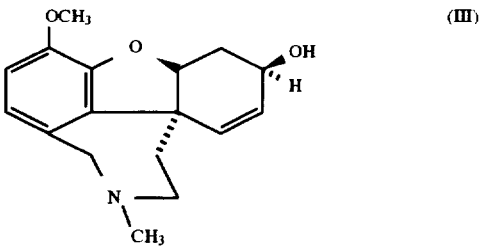

(III)

with an alkylthio salt of sodium, potassium, lithium or cesium, in butanol or pentanol at a temperature of from about 80° C. to about 135° C.

7. The process of claim 6 wherein the salt is a sodium or lithium salt.

8. The process of claim 6 wherein the salt is EtSLi or EtSNa.

9. The process of claim 6 which is carried out at from about 90° C. to about 125° C.

* * * * *

UNITED STATES PATENT AND TRADEMARK OFFICE
CERTIFICATE OF CORRECTION

PATENT NO. : 5,777,108

DATED : 07 July 1998

INVENTOR(s) : Raymond W. Kosley, et al.

It is certified that error appears in the above-identified patent and that said Letters Patent is hereby corrected as shown below:

Column 6, Lines 3 patent reads: "an active test compounds" and should read -- an active test compound --.

Column 6, Line 11 patent reads: "a reference compounds" and should read – a reference compound --.

Column 7, Line 66 patent reads: "128 – 141$^a$"" and should read – 138 – 141$^a$ – .

Column 9, Line 25 patent reads: "(6O-Demethyl)" and should read – (6-O-Demethyl) –.

Column 9, Line 59 patent reads: "chlorofonn" and should read – chloroform –.

Column 10, Line 36 patent reads: "azeotripically" and should read – azeotropically --.

UNITED STATES PATENT AND TRADEMARK OFFICE
CERTIFICATE OF CORRECTION

PATENT NO. : 5,777,108

DATED : 07 July 1998

INVENTOR(s) : Raymond W. Kosley, et al.

It is certified that error appears in the above-identified patent and that said Letters Patent is hereby corrected as shown below:

Column 11, Line 9 patent reads: "and and" and should read -- and --.

Column 15, Line 51 patent reads "dichlorofmethane" and should read -- dichloromethane --.

Column 16, Line 9 patent reads "dichlorofmethane" and should read -- dichloromethane --.

Column 17, Line 9 patent reads "solutin" and should read -- solution --.

Column 17, Line 38 patent reads "bate" and should read -- bath --.

Column 18, Line 66 patent reads "of from" and should read -- from about --.

Signed and Sealed this

Eleventh Day of April, 2000

Q. TODD DICKINSON

*Director of Patents and Trademarks*

Attest:

*Attesting Officer*